United States Patent [19]

Van Gestel

[11] Patent Number: 4,470,979
[45] Date of Patent: Sep. 11, 1984

[54] CHEMICAL STERILIZATION OF INSECTS WITH SALICYLANILIDES

[75] Inventor: Jozef F. E. Van Gestel, Vosselaar, Belgium

[73] Assignee: Janssen Pharmaceutica N.V., Beerse, Belgium

[21] Appl. No.: 506,238

[22] Filed: Jun. 20, 1983

Related U.S. Application Data

[63] Continuation-in-part of Ser. No. 419,242, Sep. 17, 1982, abandoned.

[51] Int. Cl.$^3$ ........................................... A01N 37/36
[52] U.S. Cl. .................................................... 424/230
[58] Field of Search ......................................... 424/230

[56] References Cited

U.S. PATENT DOCUMENTS 3,388,163 6/1968 Early et al. ........................ 424/230
3,721,737 3/1973 Darlington et al. ................ 424/230
4,005,218 1/1977 Janssen et al. ..................... 424/250

FOREIGN PATENT DOCUMENTS 1183641 3/1970 United Kingdom .

Primary Examiner—Allen J. Robinson
Attorney, Agent, or Firm—Geoffrey G. Dellenbaugh

[57] ABSTRACT

The invention is concerned with the use of certain salicylanilides as insect-chemosterilants and their application in the control of insect populations.

10 Claims, No Drawings

CHEMICAL STERILIZATION OF INSECTS WITH SALICYLANILIDES

CROSS-REFERENCE TO RELATED APPLICATIONS

This is a continuation-in-part of our copending application Ser. No. 419,242 filed Sept. 17, 1982, now abandoned.

BACKGROUND OF THE INVENTION

In U.S. Pat. No. 4,005,218, Brit. Pat. No. 1,183,641 and Belgian Pat. No. 796,406 there are described a range of salicylanilide derivatives which are taught to be useful as fascioliscidal and parasiticidal agents. It has now been found that a certain subclass of these compounds have valuable insect-chemosterilant properties.

DESCRIPTION OF THE INVENTION

The present invention is concerned with the insect-chemosterilant activity of a group of salicylanilide derivatives which are represented by the formula

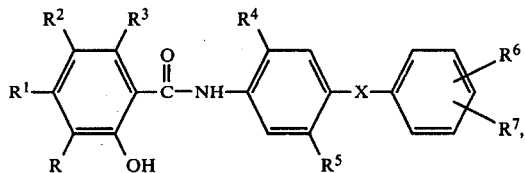

the physiologically acceptable amine addition salts and metal salts thereof, wherein:

R is a member selected from the group consisting of hydrogen, halo, lower alkyl and nitro;
$R^1$ is a member selected from the group consisting of hydrogen and halo;
$R^2$ is a member selected from the group consisting of hydrogen, halo, lower alkyl and nitro;
$R^3$ is a member selected from the group consisting of hydrogen and lower alkyl;
$R^4$ is a member selected from the group consisting of hydrogen, halo, trifluoromethyl and cyano;
$R^5$ is a member selected from the group consisting of hydrogen, halo and lower alkyl;
$R^6$ and $R^7$ are each independently from the other a member selected from the group consisting of hydrogen, halo and trifluoromethyl; and
X is a member selected from the group consisting of CO and CHCN.

As used herein, "lower alkyl" may be straight or branch chained and have from 1 to 5 carbon atoms, such as, for example, methyl, ethyl, 1-methylethyl, 1,1-dimethylethyl, propyl, butyl, pentyl and the like, and the term "halo" is generic to fluoro, chloro, bromo and iodo.

Examples of metal salts include inter alia sodium, potassium, calcium, copper and iron salts and amine addition salts include addition salts with inter alia piperidine, piperazine, N,N-diethylethanamine, N-methylglucamine, methanamine, α-methylbenzenemethanamine and 2-hydroxyethanamine.

A preferred compound within the scope of the formula (I) is N-[5-chloro-4-[(4-chlorophenyl)cyanomethyl]-2-methylphenyl]-2-hydroxy-3,5-diiodobenzamide which is generically designated as closantel. The compound is being used as an effective flukicide.

The compounds of formula (I) and their salts are generally known compounds and they may be prepared by art-known methods. Particular reference is made in this connection to U.S. Pat. No. 4,005,218, Brit. Pat. No. 1,183,641 and Belgian Pat. No. 796,406. Apart from the chemical preparation of the concerned compounds and their physical properties, the said references also disclose their useful parasiticidal activities. The compounds are taught to exhibit anthelmintic, in particular fascioliscidal activities. In U.S. Pat. No. 4,005,218 it is further indicated that the compounds possess strong activity against a number of arthropod parasites such as, for example, Oestrus ovis, Hypoderma bovis, Dermatobia hominis, Lucillia etc. All of these arthropodes are larval stages of insects that live as endo- or ectoparasites on warm-blooded animals and take their food from animal body fluids. When systemically administered to host animals, the compounds (I) are taken up in the body fluids and are thus absorbed by the parasites which are killed by the direct action of the compounds.

It has now been discovered that the compounds of formula (I) and salts thereof possess useful chemosterilant properties. When fed in appropriate amounts to adult insects they inhibit reproduction without killing the insects themselves. This sterilant activity manifests itself both on female and male insects.

Controlling and eradicating insect populations through sterilization is a highly desirable objective in view of its definite advantages in comparison with classical methods, in particular the use of insecticides. In its original way of application, the so-called male-release-technique, large numbers of sterile male insects are released in a certain area. As far as their population largely outnumbers the natural population of fertile males, the majority of the females mate with an infertile male and hence do not produce progeny. By continuously releasing sterilized males, the chances of the decreasing female population to mate with an infertile male are constantly rising and ultimately complete eradication of the pest population can be achieved.

The above techniques, while being effective and safe, nevertheless has its disadvantages, a major disadvantage being the necessity to raise, sterilize and release massive numbers of insects. It would therefore be much more attractive to sterilize the insects directly in the field by means of appropriate chemicals. Many chemosterilants have been discovered and investigated. Most of them act as alkylating agents or anti-metabolites, the toxicology of which is in general critical. Some of them have shown teratogenic, carcinogenic, mutagenic and sterilizing effects on warm-blooded animals.

The compounds of formula (I) herein have proven both effective and save. They specifically sterilize insects while being harmless to warm-blooded animals, even when administered at relatively high doses.

Without being bound by theory it is assumed, and partly deducted from experimental data, that the subject compounds interfere with the synthesis of certain specific proteins involved in the ovogenesis and spermatogenesis of the insects. The compounds are particularly useful since they exert their sterilizing effect both on female and male insects. As a consequence, upon treatment of an insect population, the chances of an untreated or ineffectively treated female to mate with an untreated or ineffectively treated male will be greatly reduced. In these circumstances a complete or nearly complete eradication of a certain insect population will be achieved much more rapidly than if only one sex would be affected.

The chemosterilant activity of the subject compounds is clearly evidenced by the results obtained in the following experiments.

The data in table I show the influence of closantel on the hatching rate of house-fly eggs at various times after treatment of females, males or both.

Table II shows the influence of various compounds of formula (I) on egg count and hatching rate at 4 days after treatment of both female and male house-flies.

TABLE I

Effect of 100 ppm closantel on the fertility of the house-fly.

| | Treatment schedule | | | |
|---|---|---|---|---|
| Day of egg collection. | Untreated males × untreated females | treated males × untreated females | Untreated males × treated females | treated males × treated females |
| 3 | 95 | 5 | —* | —* |
| 6 | 100 | 1 | 20 | —* |
| 9 | 95 | —* | 46 | —* |

—*no eggs laid.

TABLE II

Effect of 100 ppm of compounds of formula (I) on egg count and hatching rate of Musca domestica on the 4th day after treatment.

| Compound no. | Compound structure /see formula (I) | | | | | No. of eggs | % hatch |
|---|---|---|---|---|---|---|---|
| | R, $R^1,R^2,R^3$ | $R^4$ | $R^5$ | X | $R^6, R^7$ | | |
| 1 | $3,5-I_2$ | $2-CH_3$ | 5-Cl | CH(CN) | 4-Cl | 140 | 4 |
| 2* | $3,5-I_2$ | $2-CH_3$ | 5-Cl | CH(CN) | 4-Cl | 250 | 6 |
| 3 | $3,5-I_2$ | — | $3-CF_3$ | CH(CN) | 4-Cl | 500 | 11 |
| 4 | $3,5-I_2$ | — | $3-CF_3$ | CH(CN) | $3-CF_3,4-Cl$ | 550 | 14 |
| 5 | $3,5-I_2$ | — | 3-CN | CH(CN) | 4-Cl | 95 | 7 |
| 6 | $3,5-I_2$ | — | 3-Cl | CH(CN) | 4-Cl | 500 | 10 |
| 7 | $3,5-I_2$ | 2-Cl | 5-Cl | CH(CN) | 4-Cl | 600 | 13 |
| 8 | $3-NO_2,5-I$ | — | 3-Cl | CO | 4-Cl | 130 | 5 |
| 9 | $3,5-I_2$ | $2-i.C_3H_7$ | 5-Cl | CO | 4-Cl | 110 | 5 |
| Control | | | | | | 740** | 67** |

*sodium salt.
**mean values of 10 experiments.

Chemosterilant activity of test compounds in *Musca domestica* (house-fly)

1 ml of a 1% stock solution of the test compound in acetone was first diluted with 8 ml of 0.1M phosphate buffer of pH 7.5 and then added dropwise while stirring to a 7% solution of bovine serum albumin in 0.1M phosphate buffer of pH 7.5 to reach a final concentration of 100 ppm. A dilution of a placebo formulation with phosphate buffer added to bovine albumin was used as a control. 5% Saccharose was added to all test solutions. 2 ml of the test solution was pipetted on a filter-paper (diameter: 50 mm) in a petri-dish (diameter: 55 mm). Each dish was placed in a glass-jar together with 15 male or female less-than-one-day old flies. The flies were kept in the jar for 3 days and each day the test solution was renewed. After this period of treatment 15 male and 15 female flies were put together and supplied with water and dry fly food containing 45.5% of milk-powder, 45.5% of cane-sugar, 9% of autolysed yeast and 0.09% of cholesterol.

On the indicated day after the end of the treatment eggs were collected in the following standarized manner. Petri-dishes (diameter: 55 mm) were filled with small expanded clay particles, moistened with a solution of 5 g milk-powder, 5 g of beer-yeast and 5 ml of a saturated ammonium carbonate solution in 320 ml of water. One petri-dish was introduced in each fly cage.

After 6 hours the dish was removed and the eggs were collected on a series of sieves. The eggs were counted and a sufficient number (about 100) were placed on moistened black paper in a petri-dish and kept at 35° C. The rate of hatching was evaluated after one day.

In view of their potent chemosterilant activities the compounds of formula (I) may be used for the reduction and eradication of unwanted populations of various insect species, such as, for example *Ceratitis capitata* (Mediterranean fruit-fly), *Hypoderma bovine* (northern cattle grub), *Callitroga hominivorax* (screw worm-fly), *Phormia regina*, Lucillia spp. and Calliphora spp. (blow-flies), Sarcophaga spp. (flesh-flies), *Musca autumnalis* (face-fly), *Musca domestica* (house-fly), *Stomoxys calcitrans* (stable-fly), *Glossina palpalis* (tsetse-fly), etc.

In order to obtain optimal results it is important to treat an isolated population as a whole thus avoiding the penetration of new fertile specimens into the treated area. Consequently, the compounds are particularly suited for combatting insect pests in isolated areas such as, for example, closed rooms, e.g., stables, stock-houses, glass-houses, storage rooms for fruits, vegetables, cereals, fodder. Such populations may also be present in open areas where contact with other populations is greatly reduced or prevented by natural circumstances, as may be the case with isolated farms, herds or crop fields. In all circumstances it will be preferable to treat the population as a whole. Occasionally it will be advantageous to firstly reduce the population by classical means e.g. with insecticides. Depending on the circumstances such as the nature of the pest population, its habitat and the extend of the area wherein it is present, various methods of treatment may be used. In any event the active ingredient, in order to be effective, must be taken up by the insects and in general it will therefore be necessary to mix the active ingredient with or apply it to substances or products whereon the insects feed themselves. For example, compositions may be used which contain the active ingredient together with appropriate feedstuffs for the insects such as, for example carbohydrates, in particular sugars, proteins of animal or vegetable origin, amino acids, extracts etc. Various substances may be added to attract the insects. Such substances may be foodstuffs for which the insects have a specific preference or they may be specific attractants, e.g., brewer's yeast, vanillin, milk-powder, molasses, dyes, muscamone, etc. Other substances including preservatives such as, for example, benzoic acid, butylated hydroxyanisole, butylated hydroxytoluene, etc., may be added to improve the stability of the active ingredients. Particularly good results have been obtained when the substances are used in the form of a coprecipitate with protein, e.g., bovine serum albumin. In certain circumstances it may be advantageous to formulate the active ingredients in microcapsules of appropriate polymeric materials.

The chemosterilant compositions according to the invention, which may take any physical form, e.g. liquid, semi-solid (e.g. pastes) or solid (e.g. powders, granulates etc.), may be applied to specific localized areas, in particular in the form of baits, or they may be sprayed over part or all of the area to be treated e.g., by dusting, spraying, smearing, etc. Sometimes it may be appropriate to mix the active ingredients with the products or substances on which the insects are used to feed themselves. When the particular insect species involved is completely or partially feeding itself with animal body fluids, it may be appropriate to administer the compound in appropriate amounts to the host animals. Depending on the nature of the compositions and the manner and circumstances wherein they are to be used, the concentration of the active ingredient therein may vary within wide limits. In general the concentration will preferably not be lower than about 0.001% of the composition. There is almost no upper limit. For reasons of convenience and ease of formulation the concentration will in general not be higher than about 50% of the composition and preferably not higher than about 10%. Of course, higher concentrations may be warranted in concentrates or pre-mixes. Suitable compositions according to the present invention are given in the following examples which are intended to illustrate and not to limit the scope of the invention.

EXAMPLE I

Preparation of chemosterilant compositions

A. Preparation of a concentrated composition comprising 8% of N-[5-chloro-4-[(4-chlorophenyl)cyanomethyl]-2-methylphenyl]-2-hydroxy-3,5-diiodobenzamide, sodium salt. dihydrate (closantel sodium salt)

To a mixture of 75 ml of ethanol and 75 ml of 0.1M phosphate buffer ($KH_2PO_4 + Na_2HPO_4$) were added 10 g of bovine serum albumine and 1 g of closantel sodium salt and the whole was stirred until a clear solution was obtained. The solution was evaporated and the residue was dried and finely milled to yield about 12.50 g of a powdery concentrate containing 8% of closantel sodium salt (concentrate A).

The said concentrate may be used as a pre-mix for incorporation in insect food or for preparing other compositions.

B. Preparation of solid, semi-solid and liquid compositions

1. Solid composition:
A solid composition containing 100 ppm of closantel sodium salt was prepared by intimately mixing 0.125 g of concentrate A with 23.6 g of bovine serum albumine, 32 g of milk-powder, 12 g of autolysed yeast, 0.5 g of benzoic acid, 0.05 g of butylated hydroxyanisole and an amount of cane-sugar to obtain 100 g in total.

2. Paste
0.125 g Of concentrate A were intimately mixed with 30 g of polyethylene glycol 1000, 7 g of bovine serum albumin, 1 g of vanillin, 1 g of cassis extract, 10 g of polyethylene glycol, 0.1 g of muscamone, 0.05 g of butylated hydroxyanisole and glycose to obtain 100 g in total. The pasty formulation contains 100 ppm of closantel sodium salt.

3. Liquid composition:
A liquid composition comprising 100 ppm of closantel sodium salt was prepared by dissolving 0.125 g of concentrate A, 15 g of cane-sugar, 5 g of urea, 0.2 g of Xanthan gum (KELTROL F), 5 g of sodium carbonate, 5 g of bovine serum albumin and 1 g of sodium lactate in sufficient water to obtain a total volume of 100 ml.

What is claimed is:

1. A method of reducing or eradicating an insect population which comprises orally administering to said insect population a sufficient chemosterilant amount of at least one compound selected from the group consisting of

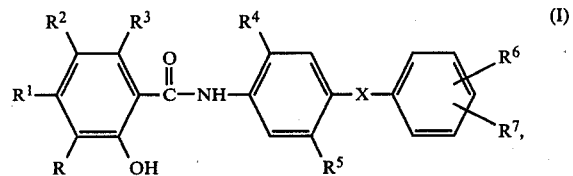

the physiologically acceptable amine addition salts and metal salts thereof, wherein:

R is a member selected from the group consisting of hydrogen, halo, lower alkyl and nitro;

$R^1$ is a member selected from the group consisting of hydrogen and halo;

$R^2$ is a member selected from the group consisting of hydrogen, halo, lower alkyl and nitro;

$R^3$ is a member selected from the group consisting of hydrogen and lower alkyl;

$R^4$ is a member selected from the group consisting of hydrogen, halo, trifluoromethyl and cyano;

$R^5$ is a member selected from the group consisting of hydrogen, halo and lower alkyl;

$R^6$ and $R^7$ are each independently from the other a member selected from the group consisting of hydrogen, halo and trifluoromethyl; and X is a member selected from the group consisting of CO and CHCN.

2. A method according to claim 1 wherein said compound is administered to said insect population in an insect bait.

3. A method according to claim 1 wherein said compound is administered to said insect population by incorporating said compound in products on which the insects feed themselves.

4. A method according to claim 1 wherein said compund is administered to said insect population by spreading a composition containing the compound over a substantial part of the population's habitat.

5. A method according to claim 4 wherein said composition is a spray.

6. A method according to claim 4 wherein said composition is a dust.

7. A method according to any one of claims 1 to 6 wherein said compound is a member selected from the group consisting of N-[5-chloro-4-[(4-chlorophenyl)-cyanomethyl]-2-methylphenyl]-2-hydroxy-3,5-diiodobenzamide, the physiologically acceptable amine addition salts and metal salts thereof.

8. A method according to any one of claims 1 to 6 wherein said insect population is a population of *Musca domestica*.

9. A method according to any one of claims 1 to 6 wherein said insect population is a population of *Stomoxys calcitrans*.

10. A method according to any one of claims 1 to 6 wherein said insect population is a population of *Ceratitis capitata*.

* * * * *